(12) United States Patent
Muller et al.

(10) Patent No.: US 7,289,654 B2
(45) Date of Patent: Oct. 30, 2007

(54) AUTOMATIC SCORING IN DIGITAL RADIOLOGY, PARTICULARLY IN MAMMOGRAPHY

(75) Inventors: Serge Muller, Guyancourt (FR); Guillaume Peter, Buc (FR); Cybéle Ciofolo, Sucy en Brie (FR)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 647 days.

(21) Appl. No.: 10/412,113

(22) Filed: Apr. 11, 2003

(65) Prior Publication Data

US 2004/0202359 A1   Oct. 14, 2004

(30) Foreign Application Priority Data

Apr. 15, 2002   (FR) ................................... 02 05165

(51) Int. Cl.
*G06K 9/00* (2006.01)
*G01D 18/00* (2006.01)

(52) U.S. Cl. ...................................... 382/132; 378/207

(58) Field of Classification Search ................ 378/207; 382/132
See application file for complete search history.

(56) References Cited

U.S. PATENT DOCUMENTS

| | | | |
|---|---|---|---|
| 5,844,964 A | | 12/1998 | Aichinger et al. |
| 6,002,433 A | * | 12/1999 | Watanabe et al. ............ 348/246 |
| 6,404,905 B1 | * | 6/2002 | Taylor, Jr. ..................... 382/128 |
| 6,497,511 B1 | * | 12/2002 | Schmitt et al. ............... 378/207 |
| 6,694,047 B1 | * | 2/2004 | Farrokhnia et al. .......... 382/132 |
| 7,027,631 B2 | * | 4/2006 | Takeo et al. .................. 382/132 |
| 2004/0202359 A1 | * | 10/2004 | Muller et al. ................. 382/131 |

OTHER PUBLICATIONS

Measures of Uncertainty: Sahnnon's Entropy located on http://mtm.ufsc.br/~taneja/book/node5.html; by Inder Jeet Taneja.*
Adel et al, "Quality control mammographic images: automated detection of microcalcification in phantom images", IWDM 2002, Toronto, CA, Jun. 11-14, 2000.

(Continued)

*Primary Examiner*—Joseph Mancuso
*Assistant Examiner*—Hadi Akhavannik
(74) *Attorney, Agent, or Firm*—Cantor Colburn LLP

(57) ABSTRACT

A method and computer program and device for evaluation of the radiographic image quality of a phantom containing cells with two visualizable objects in which: the coordinates of each phantom cell are determined on each phantom image; for each phantom cell containing at least two objects: a level of a radiographic reference signal is calculated in an area of reference at right angles with the first object whose position in the cell is known; for each area of the cell capable of containing the other object: a search area formed by a set of pixels is defined; for each pixel of the search area: a signal sample is extracted in an area of interest centered on the pixel and of the same size as the reference area; a logarithmic probability function is calculated between the sample and the reference signal, the probability function corresponding to a mathematical observer; a surface parameter of the set of probability values thus obtained is calculated; the area of interest whose surface has a peak is selected as area containing the other object; the image quality score is calculated from the results of detection for the set of phantom cells.

39 Claims, 11 Drawing Sheets

OTHER PUBLICATIONS

Karssemeijer, "Image quality in full field digital mammography", Medical Imaging and CAD, Feb. 13, 2002, pp. 1-4+, Doc. XP002255300.

Jansen et al., "Computer aided assessment of image quality for mammography using a contrast detail phantom", Medical X-ray Imaging: Impact of the new EC Directive, Malmo, SE, Jun. 13-15, 1999, vol. 90, No. 1-2, pp. 181-184.

Gagne et al., "Effect of shift invariance and stationarity assumptions on simple detection tasks: spatial and spatial frequency domains", Medicial Imaging 2001: Physics of Medical Imaging, San Diego, CA, Feb. 18-20, 2001, Proc. of the SPIE, vol. 4320, pp. 373-380.

Brooks et al., Automated analysis of the American College of Radiology mammographic accreditation phantom images, Medical Physics, vol. 24, No. 5, 1997, pp. 709-723.

Eckstein et al., "Model observers for signal known statistically tasks", Medical Imaging 2001: Image Preception and Performance, San Diego, CA, Feb. 21-22, 2001, Proc. of the SPIE, vol. 4324, pp. 91-102.

* cited by examiner

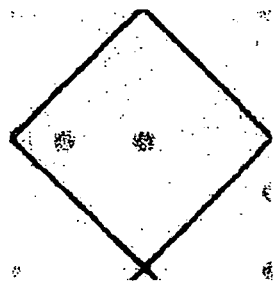
FIG_6A
FIG_6B
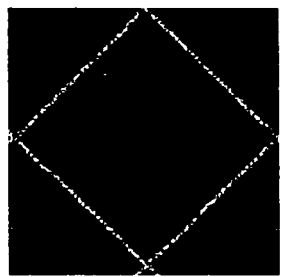
FIG_7A
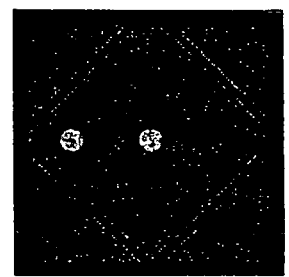
FIG_7B
FIG_8
FIG_9

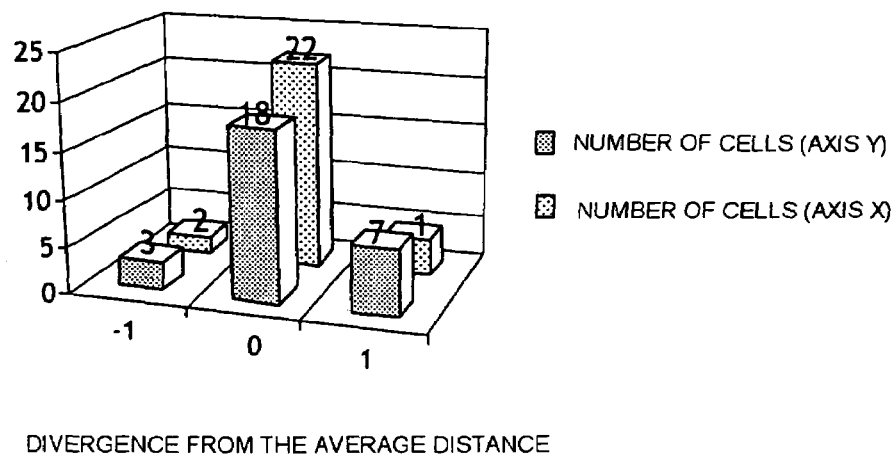
FIG_10
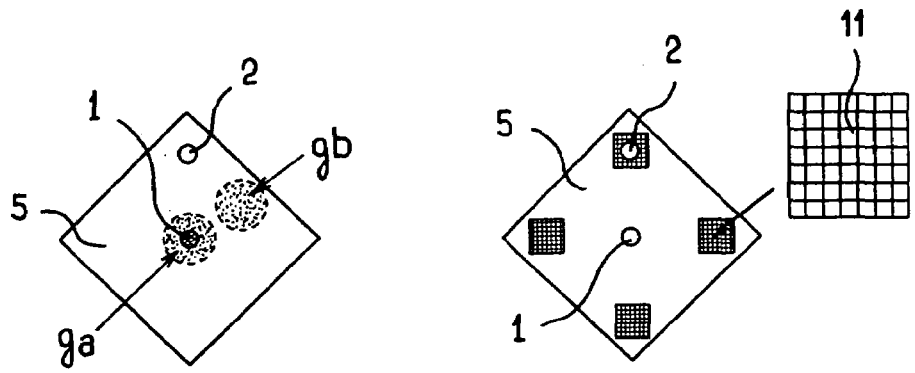
FIG_11  FIG_12

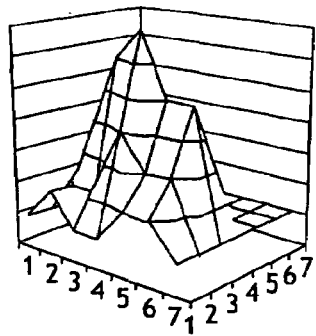
FIG_13A
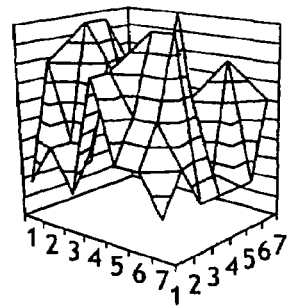
FIG_13B
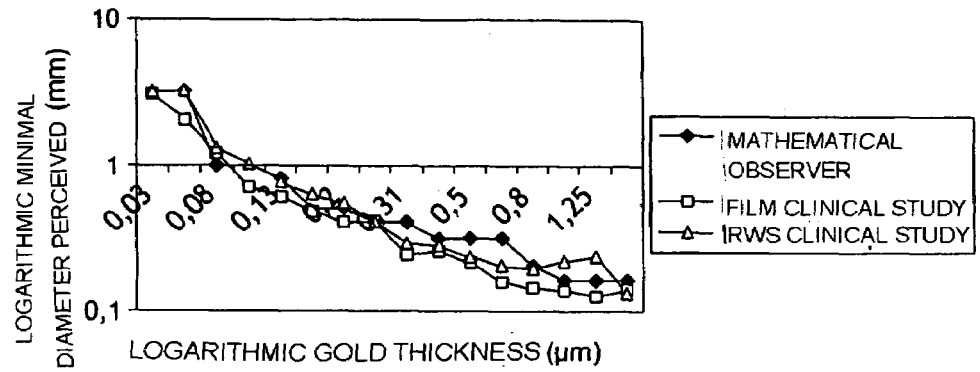
FIG_14
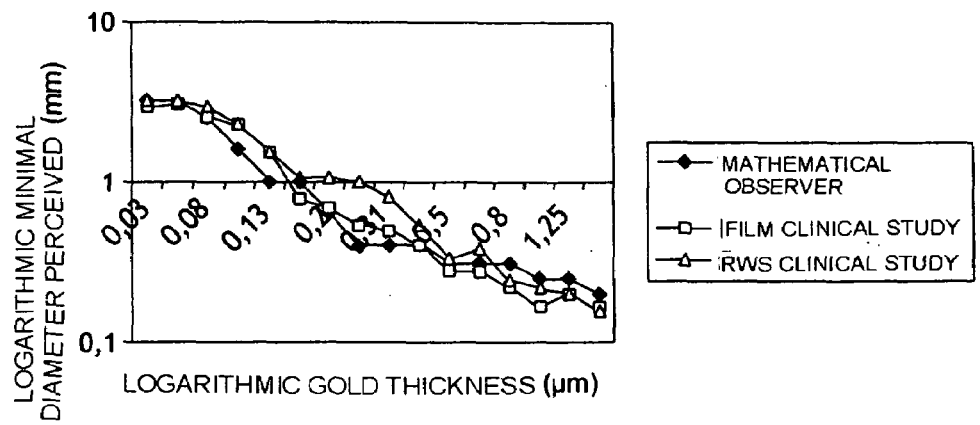
FIG_15

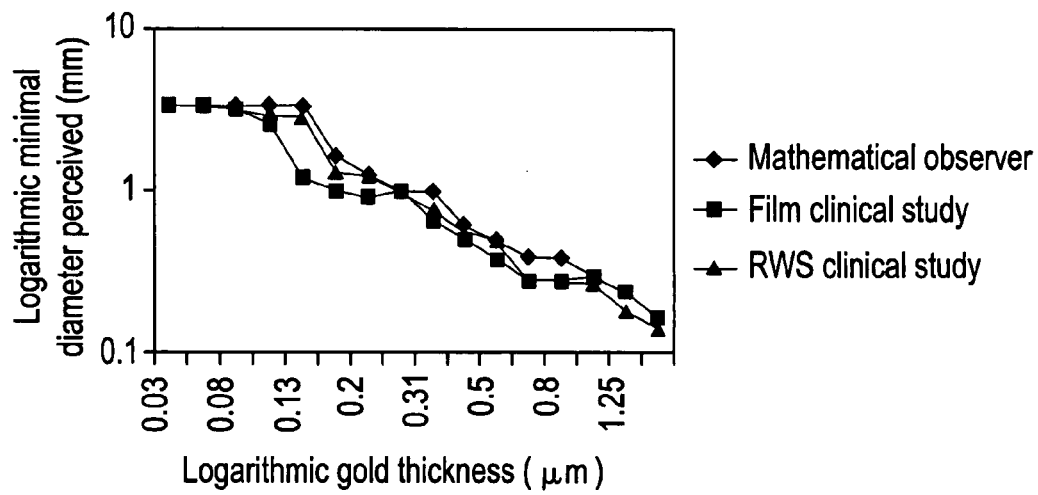
FIG. 16
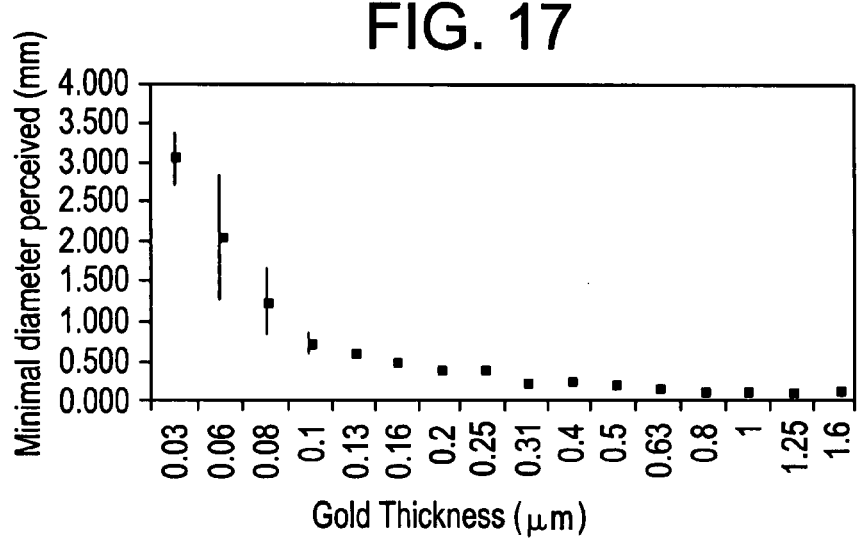
FIG. 17
FIG. 18A
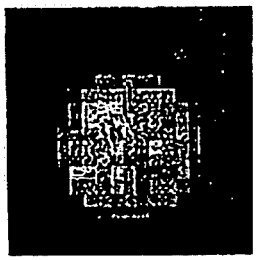
FIG. 18B
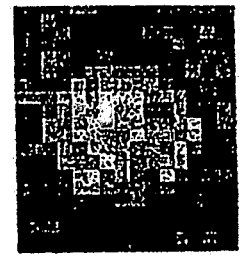

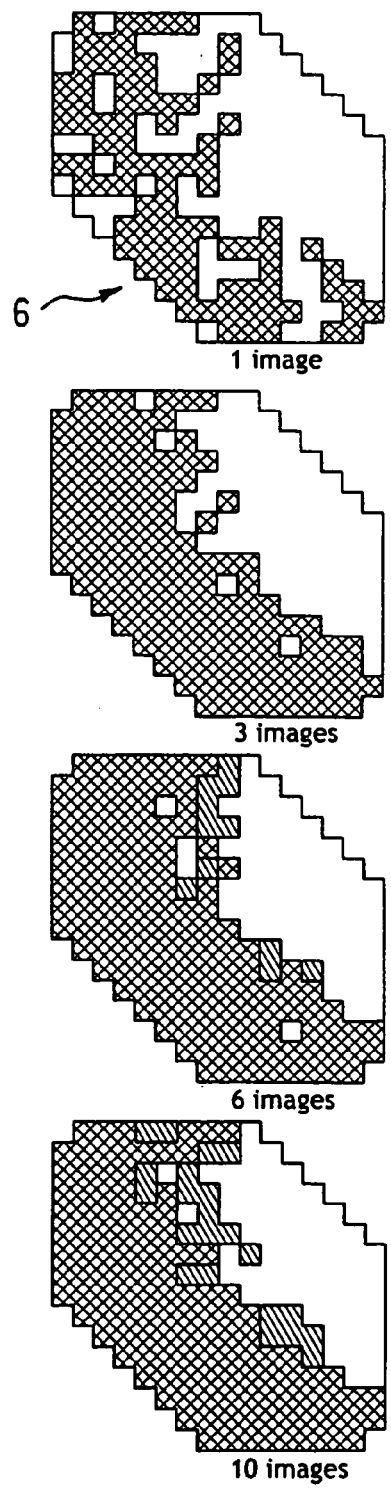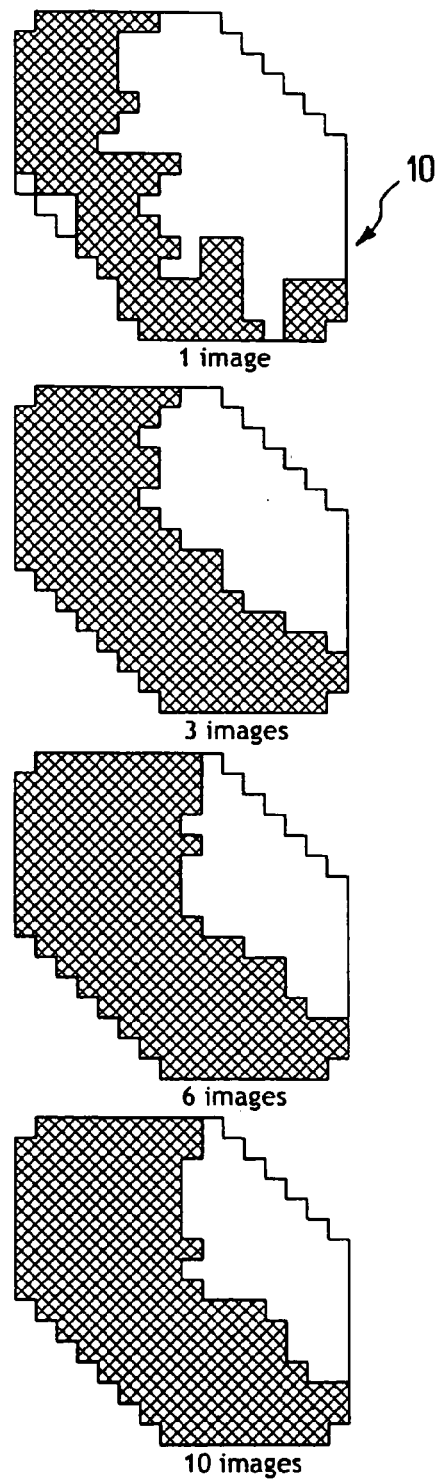
FIG_19A    FIG_19B

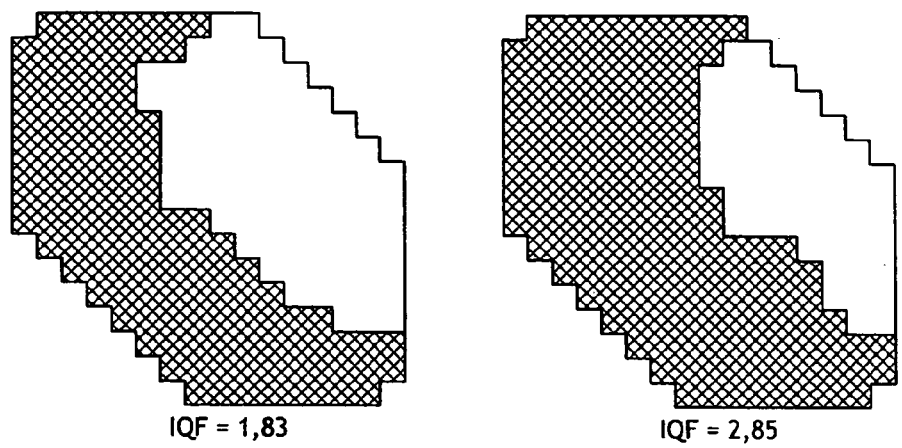
IQF = 1,83         IQF = 2,85
FIG._20A         FIG._20B
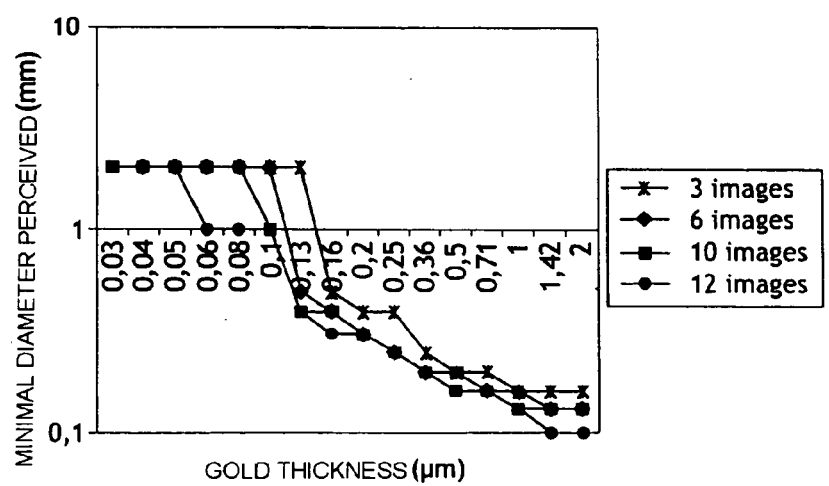
FIG._21

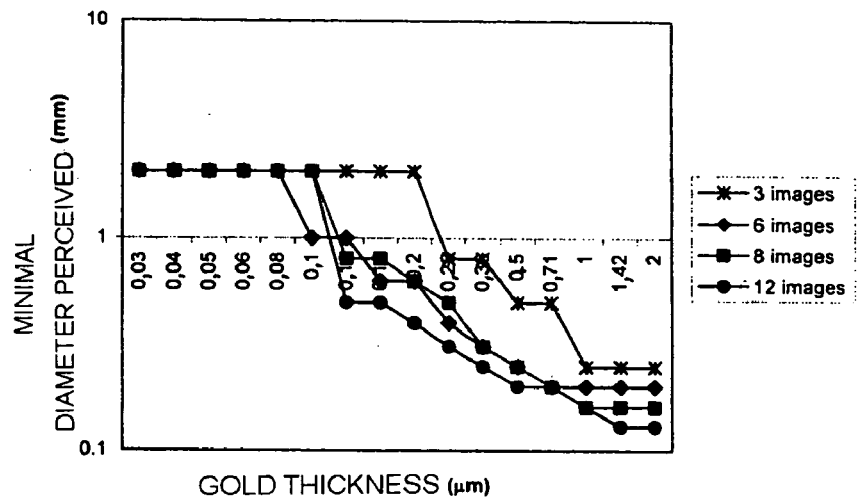
FIG_22
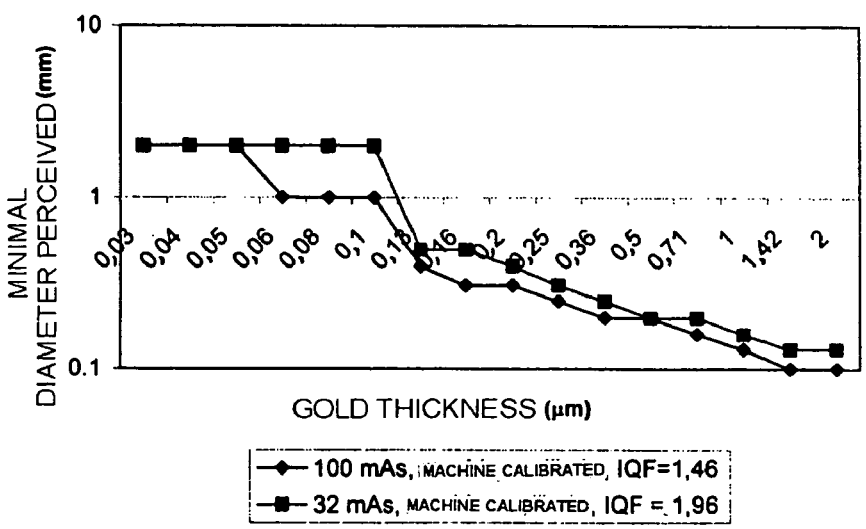
FIG_23

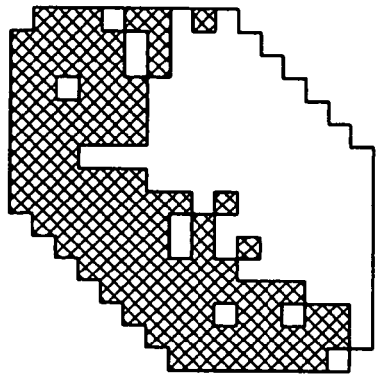 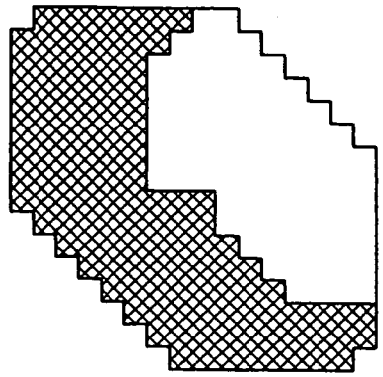
IQF = 1,78
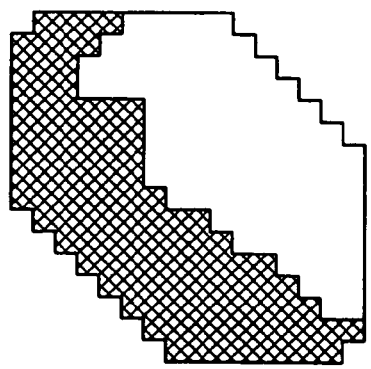 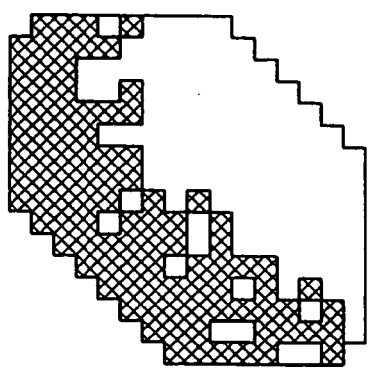
IQF = 1,46
FIG_24A  FIG_24B

AUTOMATIC SCORING IN DIGITAL RADIOLOGY, PARTICULARLY IN MAMMOGRAPHY

CROSS-REFERENCE TO RELATED APPLICATIONS

This application claims the benefit of a priority under 35 USC 119(a)-(d) to French Patent Application No. 02 05165 filed Apr. 15, 2002, the entire contents of which are hereby incorporated by reference.

BACKGROUND OF THE INVENTION

The present invention concerns a method and device for evaluation of the quality of an image in digital radiology, particularly in mammography.

In particular, it concerns a method of "pointage" (or "scoring" according to the English-language terminology generally used by one skilled in the art of areas of interest on a digital radiological image of a phantom object.

One of the methods of evaluation of image quality is phantom scoring. An image on which objects of interest appear is presented to an observer. The observer then indicates the number of objects he/she manages to see as well as their location. The operation can be repeated with different observers of different images. A score is established from the results obtained. The method makes it possible to give a quality measurement of the entire image acquisition chain.

On the other hand, observation of the phantom image is an activity close to diagnosis on a real image, which makes it possible to link the idea of quality with that of a clinical task.

Scoring according to the prior art presents some drawbacks.

One of the drawbacks of scoring is inter- and intra-observer variability. In fact, fatigue and the experience of the observers can strongly influence the results.

Furthermore, manual scoring is tedious and lengthy. The users of digital radiography apparatuses tend not always to engage in scoring when it is necessary.

BRIEF DESCRIPTION OF THE INVENTION

An embodiment of the invention is a scoring method that makes it possible to give a quality measurement of the image acquisition chain of a digital mammography apparatus or of another radiography apparatus by overcoming the phenomenon of inter- and intra-observer variability.

An embodiment of the invention is to propose a method of automatic scoring. An embodiment of an automatic scoring method, in which the observer is no longer human but mathematical, makes it possible to secure constant performances when the test is performed with the same image or the same set of images.

An embodiment of the invention is to propose an automatic scoring method that delivers a score close to the score obtained by a manual scoring carried out by human observers.

An embodiment of the invention is to propose an automatic scoring method that makes it possible both to reduce variability between observers and the time it takes to obtain results. Scoring is therefore carried out more easily and more willingly by the users of apparatuses.

In an embodiment the invention proposes a method of evaluation of the quality of at least one radiographic image of a phantom containing a plurality of cells, at least one of which contains two objects visualizable by radiography, the position in the cell of at least one of the objects being known, and the position in the cell of the other object being random from one cell to another, in which:

the coordinates of each phantom cell are determined on each phantom image;

for each phantom cell containing at least two objects:

a level of a radiographic reference signal is calculated in an area of reference at right angles with the first object whose position in the cell is known;

for each area of the cell capable of containing the other object:

a search area formed by a set of pixels is defined;

for each pixel of the search area:

a signal sample is extracted in an area of interest centered on the pixel and of the same size as the reference area;

a probability parameter is calculated between the sample and the reference signal, the probability function corresponding to a mathematical observer;

a parameter characterizing the trend of the representative surface of the set of probability values thus obtained is calculated;

the area of interest whose surface presents the trend of a peak is selected as area containing the other object;

the image quality score is calculated from the results of detection for the set of phantom cells.

The method may further comprise the following, taken alone or in any of their technically possible combinations:

when it is desired to evaluate the quality of a set of images, after selection of the area containing the minimal entropy and before calculation of the image quality score, it involves the steps:

a proportion of correct detections is calculated from a set of processed images;

the confidence interval is calculated around that proportion of correct detections;

a detection is declared valid if the lower limit of the confidence interval is higher than a threshold value;

standard rules of correction of the phantom are used;

in order to obtain the level of the radiographic reference signal:

the reference area of the image containing the first object is selected by centering it on the center of the object, the diameter of the reference area being slightly greater than that of the object;

a background area of the image is selected of the same size as the reference area on a region of the cell that can in no case contain any object;

an overall average is taken of the signals selected for each of these areas;

the average signal of the background area is subtracted from the average signal of the reference area;

the probability parameter is a logarithmic probability function corresponding to a non-whitening observer on the search area, said function being defined by the formula:

$$\lambda_{NPW}(g) = (\bar{g}_a - \bar{g}_b)^t g,$$

where g is the signal of the image sample in the search area $\bar{g}_a$ is the average signal of the reference area and $\bar{g}_b$ is the average signal of the background area;

the parameter characterizing the trend of the surface is an entropy parameter, which is defined for each area k by the formula $$h_k = \sum_{i,j=1}^{L} \lambda_{i,j,norm} \log_2(\lambda_{i,j,norm}), \text{ where } k \in \{1, \ldots, N\}.$$

where k is the reference of the area of the cell capable of containing the other object, $\lambda_{i,j,norm}$ is the standardized logarithmic probability value calculated for the pixel (i, j) of the search area and L is the number of pixels of the search area;

the limits of the confidence interval are calculated by the formula:

$$IC = \frac{X + k^2/2}{n + k^2} \pm \frac{kn^{1/2}}{n + k^2}\left(\hat{p}(1 - \hat{p}) + \frac{k^2}{4n}\right)^{1/n},$$

where X is the number of correct detections among the n images processed, $\hat{p}$ is the proportion of correct detections, n is the number of images processed and k is the standard normal deviation;

a value of 1.96 is assigned to the standard normal deviation corresponding to the calculation of 95% confidence intervals;

the value of 0.25 is assigned to the threshold value; and at least one image of a phantom containing two chips in each cell is observed, the cells being rectangular, a first chip being situated in the center of each cell, the other chip being randomly situated from one cell to the other in one of the four corners of each cell.

The invention also concerns a device for use of a method according to embodiments of the invention, notably on a radiographic image acquisition device.

The invention also concerns a computer program support that contains program means for use in the method.

BRIEF DESCRIPTION OF THE DRAWINGS

The invention will be better understood from the following description, which is strictly illustrative and not limitative and should be read with reference to the attached drawings in which:

FIG. 6A is a schematic representation of a "raw" image;

FIG. 6B is a schematic representation of an image of the grid;

FIG. 7A is a schematic representation of an inverted image of the image according to FIG. 4;

FIG. 7B is a schematic representation of an image according to 7A reduced from an image without the grid according to FIG. 6B;

FIG. 8 is a schematic representation of an image according to FIG. 7B which was thresholded;

FIG. 9 is a schematic representation of an image according to FIG. 8 of ultimate eroded type;

FIG. 10 represents in graph form the distribution of distance between the centers of the chips of a phantom cell;

FIG. 11 is a schematic representation of the location of signal and background areas on a phantom cell;

FIG. 12 is a schematic representation of the location of search areas for the position of the center of chip No. 2;

FIGS. 13A and 13B schematically represent in graph form a trend of the probability ratio as a function of the position of a pixel in a cell;

FIGS. 14 to 16 represent in the form of curves a comparison of the values of minimal diameter perceived as a function of the thickness of gold of the chips, for scoring methods according to an embodiment of the invention or manual scoring methods, and for different image acquisition parameters;

FIG. 17 represents in curve form an inter-observer variability for the parameters 100 mAs and 45 mm of Plexiglas;

FIG. 18A is a schematic representation of an extracted center chip of an image;

FIG. 18B is a schematic representation of a center chip of the average of a set of six images;

FIG. 19A is a schematic representation of results obtained by a non-whitening filter (100 mAs, 45 mm of Plexiglas), before correction;

FIG. 19B is a schematic representation of results obtained by a non-whitening filter (100 mAs, 45 mm of Plexiglas), after correction;

FIG. 20A is a schematic representation of results in cells well detected on all the images;

FIG. 20B is a schematic representation of results in cells well detected with a new decision criterion;

FIGS. 21 and 22 show in graphic form the influence of the number of images (32 mAs, 45 mm of Plexiglas) on the minimal diameter perceived as a function of the thickness of gold;

FIG. 23 represents the performances of a non-whitening filter with 45 mm of Plexiglas, 12 images for two different doses;

FIGS. 24A and 24B show schematically the influence of calibration of the apparatus (12 images, 100 mAs, 45 mm of Plexiglas);

DETAILED DESCRIPTION OF THE INVENTION

The invention will be described below by means of an example. It is well understood that the principle of the method described has numerous other applications throughout the field of radiology and the example chosen does not limit the range of protection.

For the establishment of an example of a scoring method according to an embodiment of the invention, a phantom identical to the phantom used in the methods of the prior art is used. Of course, any phantom can be used, with any number of cells and also any number of visualizable objects. The cells can thus also take any shape.

Figure 1A:
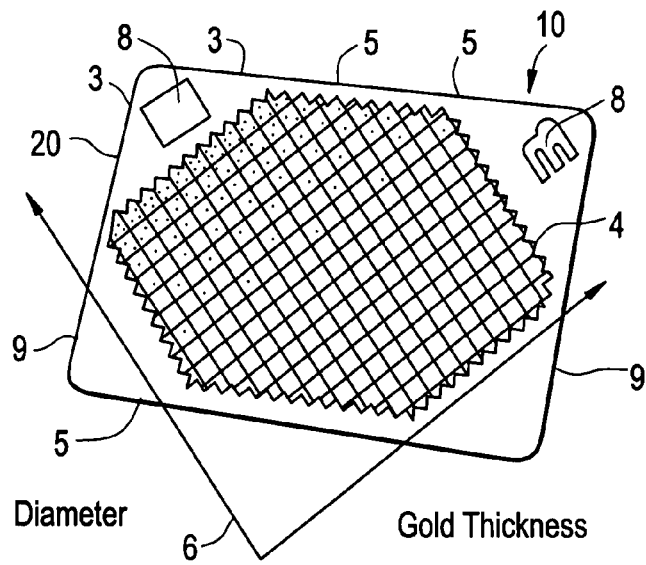
FIG. 1A is a schematic representation of a CD MAM phantom.

FIG. 1A is a schematic representation of a phantom for the marking of details and of contrast in mammography or CD MAM (Contrast-Detail Mammography according to the English-language terminology generally used by one skilled in the art 10 employed in a method according to an embodiment of the invention.

The CD MAM phantom ordinarily used in mammography comprises of an aluminum plate 20 that is 0.5 mm thick, on which gold chips 3 of variable diameter and thickness are fastened.

The chips 3 can be arranged in an array 4 of 16 rows and 16 columns. As the orthogonal marker 6 schematically represented on the edge of the phantom 10 in FIG. 1A shows, the chips 3 of the same row can have a constant diameter, and those of the same column can have a constant thickness. Each cell 5 of the array can contain two (or more) identical chips 3.

Figure 1B:
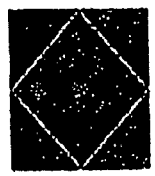
FIG. 1B is a schematic representation of a radiological image of a cell of a phantom according to FIG. 1A.

As FIG. 1B shows, one of the chips 3 is situated in the center of the cell 5, and the other is in one of the corners. The choice of corner is random. In the course of the description, for a given cell, the center chip will be called "chip No. 1" and the corner chip will be called "chip No. 2".

With reference again to FIG. 1A, a film transparent to X-rays is placed beside the aluminum plate 20. A grid 7 embodying the array 4, the information 8 on the phantom 10 and the diameter and thickness values 9 of the chips 3 for each row and each column are printed on that film by means of a very thin paint. These elements therefore appear with a marked contrast on the radiological images.

Everything is inserted in a Plexiglas plate 5 mm thick.

Table 1 presents the thicknesses and diameters of the chips of phantoms 3.2 or 3.4.

TABLE 1

Characteristics of the gold chips 3 of CD MAM 3.2 and 3.4 phantoms 10

| | Thickness (μm) | | | Diameter (μm) | |
|---|---|---|---|---|---|
| Column | 3.2 | 3.4 | Row | 3.2 | 3.4 |
| 1 | 0.05 | 0.03 | 1 | 0.10 | 0.06 |
| 2 | 0.06 | 0.04 | 2 | 0.13 | 0.08 |
| 3 | 0.08 | 0.05 | 3 | 0.16 | 0.10 |
| 4 | 0.10 | 0.06 | 4 | 0.20 | 0.13 |
| 5 | 0.13 | 0.08 | 5 | 0.25 | 0.16 |
| 6 | 0.16 | 0.10 | 6 | 0.31 | 0.20 |
| 7 | 0.20 | 0.13 | 7 | 0.40 | 0.25 |
| 8 | 0.25 | 0.16 | 8 | 0.50 | 0.31 |
| 9 | 0.31 | 0.20 | 9 | 0.63 | 0.40 |
| 10 | 0.40 | 0.25 | 10 | 0.80 | 0.50 |
| 11 | 0.50 | 0.36 | 11 | 1.00 | 0.63 |
| 12 | 0.63 | 0.50 | 12 | 1.25 | 0.80 |
| 13 | 0.80 | 0.71 | 13 | 1.60 | 1.00 |
| 14 | 1.00 | 1.00 | 14 | 2.00 | 1.25 |
| 15 | 1.25 | 1.42 | 15 | 2.50 | 1.60 |
| 16 | 1.6 | 2.00 | 16 | 3.20 | 2.00 |

Calculation of Score

A scoring method according to an embodiment of the invention uses a calculation of the score. This score calculation method is recommended by the manufacturers.

On a scoring test, observers are presented with a radiological image of the phantom 10. They must indicate, for each cell 5, in what corner the gold chip No. 2 is located. For that purpose, they have a diagram of the array 4 available, on which they can note the positions observed and leave empty the cells 5 for which they do not manage to give a response.

Reading of the results makes it possible to fill a new array. A "T" corresponds to a cell for which the position of chip No. 2 has been correctly identified, an "N" to an absence of response and an "F" to a poor response. Some rules of correction making it possible to eliminate the good responses due to chance are then applied.

According to those rules of correction, each cell is then examined. As a function of its neighbors before application of the correction algorithm, it is determined whether its code is retained or modified. For that purpose, the rules set forth below can be used.

Principal Rules
  for a phantom cell to be noted "T", it must have at least two neighbors noted "T";
  a chip noted "N" will be noted "T" if it has 3 or 4 neighbors noted "T".

Exceptions to the Principal Rules
  a cell noted "T" which has only two neighbors (on the edge of the phantom) will retain its code if it has at least one neighbor noted "T";
  a cell noted "N" or "F" which has only two neighbors will be noted "T" if its two neighbors are noted "T";
  the empty corners of the phantom are noted "T" if their two neighbors are noted "T".

Finally, the results can be analyzed in order to obtain a score. A frequent measurement is the Image Quality Factor or IQF. That factor is calculated as follows:

$$IQF = \sum_{i=1}^{16} C_i D_{i,\min},$$

where $D_{i,min}$ is the minimal diameter perceived in the $i^{th}$ column, which corresponds to a gold thickness $C_i$.

It is understood that the lower the IQF value, the better the image quality.

Other Image Quality Factors

The IQF is a value which makes it possible to give an overall score, but which does not show on what regions of the phantom the observer's performances are good. A simple graphic representation makes it possible to have a more precise knowledge of the results obtained.

Figure 2:
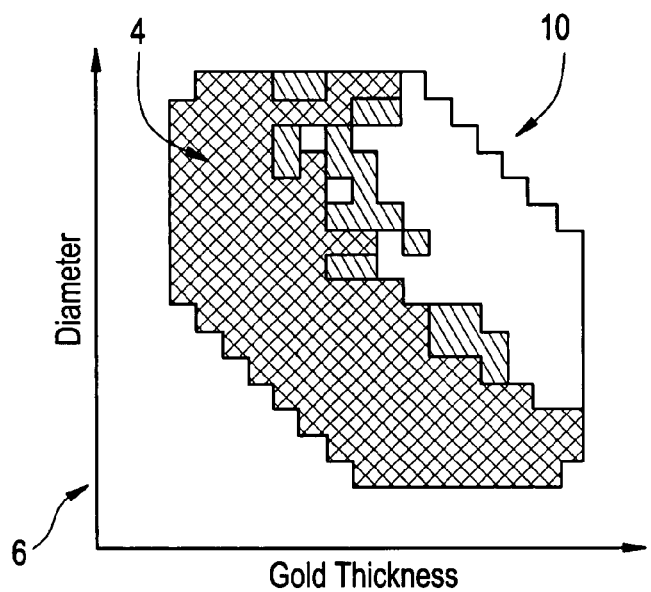
FIG. 2 is a graphic representation of the performances of the observer.

FIG. 2 is an example of such a graphic representation of the observer's performances.

In FIG. 2, the phantom 10 of FIG. 1A is represented by the set of white and hatched boxes of the array 4. The white boxes correspond to the cells for which the detection of chip No. 2 has been correctly made. The single-hatched boxes correspond to the cells for which the detection is correct in some cases (generally more than 70% of the images processed) and the double-hatched boxes correspond to the other cells.

Furthermore, in link with the IQF, it may be useful to trace the curve of the minimal diameter perceived (or correctly detected) as a function of the thickness of gold. The less the values of points of that curve, the more likely it is that the observer's performances will be good. However, as can be seen on some of the columns of FIG. 2, it so happens that large-diameter chips will not be detected correctly. The course of the curve of minimal diameter perceived as a function of thickness of gold gives additional information in that case. The lower the values of points of that curve, the wider the correct area of detection of the phantom.

USE OF THE METHOD ACCORDING TO AN EMBODIMENT OF THE INVENTION

This part of the description first presents the constraints on use of the automatic scoring algorithm and then the algorithm itself.

In order to understand well the conception of scoring algorithm, it is necessary to present certain essential points.

First of all the choice of type of images processed is going to be presented. In fact, the scoring algorithm can be applied on images (of "raw" type according to the English-language terminology or "processed" also according to the English-language terminology). The images observed by radiologists are of "processed" type. In the case of mammograms, these are images on which the contrast has been modified at the edge of the breast, so as to afford better visibility of the structures. That processing is advantageous for the human eye, when clinical images are processed, but is of no interest when images of phantoms of uniform thickness are involved. A preliminary study carried on by the inventors made it possible to show that the automatic scoring results were similar on images of both types. It will therefore be implemented on "raw" images in order to reduce the calculation time.

The choice of the mathematical observer is then going to be presented. In fact, the choice of an observer depends both on performances and the constraints it imposes on development of the test. It is sought to obtain a mathematical observer making it possible to evaluate the quality of a phantom image. It must therefore be sensitive to variations of diameter and thickness of the gold chips and its behavior must be similar to or at least correlated with that of human vision.

On first approach, the Bayesian ideal observer, the Hotelling observer and the non-whitening filter ("Non Pre-Whitening Matched Filter" noted NPW in the description below) have been implemented, in order to compare their performances and to select the one best suited to scoring of the phantom. Each of those observers presents advantages a priori: the ideal observer is well suited to the case of Known Signal/Known Background, the Hotelling observer gives results closer to those of the human visual system, and the non-whitening filter is remarkable for its simplicity.

The principle of these observers being founded on the hypothesis of a Gaussian signal embedded in a Gaussian noise, it is necessary to have several versions of the phantom image available. Thus, according to the central limit theorem, the conditions will approach the ideal case. Nevertheless, it must be possible to carry out the test in the case of regular quality control and therefore limit the number of images to be acquired. The choice of observer will depend on the number of images necessary to obtain satisfactory results.

The following three logarithmic probability functions were calculated:

$$\lambda_{idt} = (\bar{g}_a - \bar{g}_b)^t C_n^{-1} g,$$

$$\lambda_{Hot} = (\bar{g}_a - \bar{g}_b)^t S^{-1} g,$$

$$\lambda_{NPW} = (\bar{g}_a - \bar{g}_b)^t g,$$

where $C_n$ and $S$ are covariance matrices, g is the image sample signal in the search area, $\bar{g}_a$ is the average signal of the reference area and $\bar{g}_b$ is the average signal of the background area.

For the ideal observer, the covariance matrix is defined by the classic equation:

$$C_p = \overline{(g - \bar{g})(g - \bar{g})^t}$$

For the Hotelling observer, the covariance matrix S used is the arithmetical mean of the two covariances matrices noted $C_{g1}$ and $C_{g2}$ in each class considered (signal present, signal absent), namely:

$$S = \frac{1}{2}(C_{g1} + C_{g2}) \text{ and}$$

$$C_{gk} = \overline{(g - \bar{g}_k)(g - \bar{g}_k)^t}$$

The ideal observer and the Hotelling observer need the calculation and inversion of these matrices. Now, as the use of a real image does not correspond to an ideal case, they are poorly conditioned. The digital method of decomposition by singular values can therefore be used to undertake inversion. That considerably increases the calculation time by reason of the number of cells in the phantom.

This preliminary study made it possible to show that the choice of ideal and Hotelling observers contributed no decisive advantages in terms of performance compared to the non-whitening filter. All of the results presented below in the description therefore concern the non-whitening filter.

The automatic detection of the position of the cells is then going to be presented.

Figure 3A:
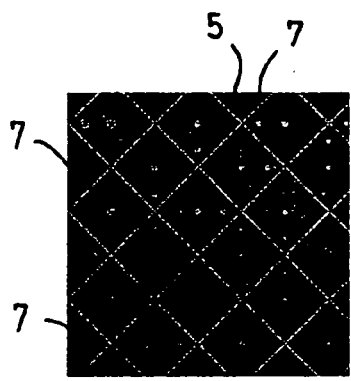
FIG. 3A is a schematic representation of a phantom sample.
Figure 3B:
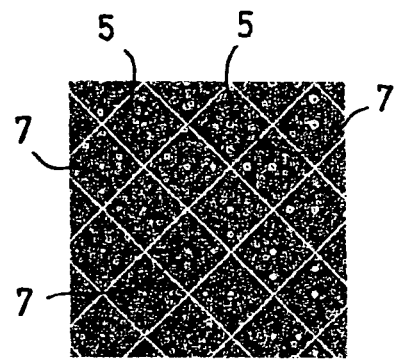
FIG. 3B is a schematic representation of the image subtracted after application of a top-hat type filter.

Just like human observers, the automatic scoring algorithm processes the cells 5 of the phantom 10 separately. It is therefore necessary to locate them precisely. For that purpose, the grid 7 is detected by means of simple mathematical morphology operators. The grid 7 comes in the form of highly contrasted rows, inclined ±45°. The stages of detection are:

1. Image preprocessing. The principal preprocessing operations are schematically represented in FIGS. 3A and 3B. An acquired image of FIG. 3A is thus taken, on which top-hat morphological filtering is carried out with a square structural element of 10 pixels per side, in order to eliminate the chips and other small-sized contrasted elements on the image. The contrast is then accentuated by a histogram equalization. An image according to FIG. 3B is obtained.

Figure 4A:
FIGS. 4A and 4B are schematic representations of an image after opening by linear structural elements inclined approximately 45°.
Figure 4B:

2. Detection of lines at +45°. The principal detection operations are schematically represented in FIGS. 4A and 4B. An image of FIG. 3B is thus taken, on which a morphological opening of the image is made by a segment of 40 pixels inclined ±45°. The image obtained presents lines inclined ±45° on a background of variable gray levels. A threshold value of that new image is calculated, for example:

Threshold=min(image)+0.6(max(image)−min(image)).

The image is then rendered binary: all the pixels whose gray level is higher than threshold are placed at 1, and the others at 0. The image obtained, visible in FIG. 4A, in which the lines now appear in white on a black background, is kept in memory.

3. Detection of lines at −45°. The same operations are carried out to arrive at an image presenting white lines on a black background inclined −45°. That image is visible in FIG. 4B.

Figure 5:
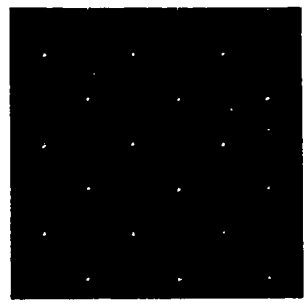
FIG. 5 is a schematic representation of the image of the intersections of the grid.

4. Location of intersections of the grid. A logic "AND" is formed between both images of FIGS. 4A and 4B stored in stages 2 and 3. The image obtained, visible in FIG. 5, presents small groups of white pixels at each intersection of the grid 7.

5. Extraction of the coordinates of each cell 5. The coordinates of each cell 5 are approximately known. It is then searched in a window situated nearly at the center of the image of FIG. 5 whether an intersection is actually present. If that is not the case, one searches in a second window. If the result is still negative, the acquisition has not been made correctly. Otherwise, the coordinates of each cell are found by taking an average on each group of white pixels. If an intersection does not appear (by reason of overly selective thresholding, for example), the a priori knowledge of the phantom 10 is used to find the coordinates as a function of those of the neighboring cells 5. The coordinates of the upper corner of each cell 5 are therefore obtained.

With these coordinates, the algorithm can cover the whole image of the phantom in order to carry out the scoring.

Finally, the variation in size of chips is going to be taken into account.

In order to conduct this study, two versions of the CD MAM phantom 10 are available: versions 3.2 and 3.4. As Table 1 shows, the sizes of the chips 3 are very different. It can, notably, be observed that in the case of version 3.4, the chips 3 of the first three rows of the array 4 have a diameter less than or equal to 100 microns. Now, the size of a pixel of the image originating from the digital detector of the Senograph™ 2000D, for example, is also 100 microns. Consequently, the location of the small-sized chips must be precisely determined in order to obtain good results at the detection level.

A preliminary study on a highly contrasted "raw" image of the CD MAM phantom 10 made it possible to evaluate the distance between the centers of the chips 3 of different cells 5. For that purpose, the following processing was applied to each cell 5:

1. Detection of the rows corresponding to the grid 7 on the "raw" image visible in FIG. 6A and noted im1, with a method identical to that described in the preceding section for the detection of intersections of the grid 7. The structural element used for preprocessing of the image is a square of 10 pixels per side. The size of the linear structural element is 20 pixels and the threshold value is 0.4. An inverted binary image noted im2 and visible in FIG. 6B is obtained.

2. Inversion of the gray level of the initial image im1 in order to obtain an image visible in FIG. 7A and elimination of the areas corresponding to the white areas of the binary image im2 of FIG. 6B, that is, at the edge of the image and at the rows of the grid in order to obtain an image according to FIG. 7B.

Remark: The gray levels of the background and of the chips are identical for both images 7A and 7B.

3. Translation of the gray levels and thresholding in order to render the image binary. The threshold value is set case by case. An image according to FIG. 8 is obtained.

Remark: Some residues of the grid can be observed, but they are far enough from the chips not to jeopardize the continuation of processing.

4. Calculation of ultimate eroded part, with a structural element of connexity 4. An ultimate eroded part consists of the result of successive erosions in the course of which only the particles disappearing between two erosion stages are retained. Working in connexity 4 comprises of considering only the 4 pixels neighboring the pixel running in the east, west, north and south directions, when working on square pattern images. The ultimate eroded part of the image consists of two groups of pixels corresponding to the two centers of the chips, as well as the residues mentioned above. In the best of cases, each of the groups is reduced to a single pixel. The ultimate eroded part is visible in FIG. 9.

Calculation of the distance between the centers of the chips 3 from the average coordinates of the ultimate eroded parts of the chips.

Twenty-eight cells situated in a highly contrasted area of the image and presenting chips 3 of variable diameter were processed. The average distance between the centers of the chips 3 of the same cell is forty-four pixels along an axis and nil along the orthogonal axis. FIG. 10 shows the distribution of cells 5 as a function of their divergence from the average distance.

One finds in FIG. 10 that, for each of the axes, the distance between the centers of the chips has a variance less than one pixel (0.45 along axis x and 0.57 along axis y). Nevertheless, considering that it is not strictly constant, a method making it possible to locate chip No. 2 was implemented in the automatic scoring algorithm.

Description of the Algorithm Employed

The algorithm making it possible to locate chip No. 2 is now going to be described. Once the coordinates of the cells 5 of the phantom 10 have been calculated, each is processed separately. On each cell 5 the observer has the reference chip available, chip No. 1, situated in the center. It must then indicate in what corner an identical chip is to be found, chip No. 2.

This case comes within the area of signal detection. The two hypotheses $H_a$ and $H_b$ correspond respectively to the cases of "Corner with chip No. 2" and "Empty corner." Referring to the theory of detection, it is considered that a corner with chip will consist of signal, background and noise, while an empty corner will contain only the background and noise. Throughout this description, the term "overall average" designates an average taken on all of the images processed upon execution of the algorithm. These images were acquired just once, with the same acquisition parameters and without moving the phantom 10.

For each cell 5, the principle of detection is as follows. The main stages are schematically represented in FIG. 11.

Construction of a Reference Signal:

1. Extraction of a signal area: a round area of the image is selected in the center of the cell. That area contains the chip 1, or reference signal, and it is noted $g_a$. Its diameter is slightly greater than that of chip 1.

2. Extraction of a background area alone: a round area of the same size is selected on a region of the cell that can in no case contain any chip. That area consists of background and is noted $g_b$.

3. Averaging: an overall average is taken for each of those areas. The vectors $\bar{g}_a$ and $\bar{g}_b$ are obtained.

Processing of the Corners of the Cell

Gold chip No. 2 of the cell 5 is found in one of the four corners. To apply the probability function of the mathematical observer, a sample to be tested must be available, that is, a round area of the same size as the reference signal, extracted in one of those corners. The probability function will be maximal, when the sample tested is similar to the reference signal; in other words, when it contains the signal emanating from chip No. 2 correctly centered in the round area. Now, some chips 3 are so small that the signal they generate can occupy only one pixel of the image. In that case, the location of the area extracted must be very precise in order to guarantee good centering of the signal. In order to take that constraint into account, FIG. 12 shows that a square region 11 of six pixels per side is defined around the presumed center of chip No. 2.

For each corner of the cell, and for each pixel of the corner search area, noted pixel P, the following operations are performed:

1. Extraction of the areas to be processed: a round area is selected, of the same size as the area which served to construct the reference signal, centered on pixel P.

2. Application of the probability function: The probability function corresponding to the observer is applied on that area. This function is calculated from reference signals $\bar{g}_a$ and $\bar{g}_b$ (for the non-whitening filter, it is a question of function $\lambda_{NPW}(g)=(\bar{g}_a-\bar{g}_b)'g$. Of course, other probability formulas are possible. Other formulas can thus be used for calculation of the probability parameter, notably, the probability formulas corresponding to other mathematical observers and, notably, those already mentioned above in this description. It can thus be stated that probability expresses a correlation between the sample and the reference signal.

3. The result is stored in the memory means of the apparatus.

Choice of Corner Containing the Chip

For each of the four corners of the cell, forty-nine logarithmic probability ratio values are available. The choice of corner containing chip No. 2 takes all those values into account.

Once the calculations are finished, the number of corners chosen for each cell of each image processed are stored in one or more files in order to be able to access them to process the results statistically.

Calculation of the Proportion of Correct Detections.

For each cell 5, the corner chosen is compared with the corner really containing the chip. The proportion of correct detections out of the set of images processed is calculated.

The method can thus be recapitulated.

Detection of coordinates of the cells 5

For each cell 5:

Construction of the reference signal $\bar{g}_a-\bar{g}_b$

For each corner:

For each pixel P of the search area associated with the corner

Extraction of a sample g centered on the pixel P

Calculation of the logarithmic probability ratio $\lambda_{NPW}(g)=(\bar{g}_a-\bar{g}_b)'g$, Calculation of entropy on the values of $\lambda$ Choice of corner: the one containing chip No. 2 is the one with the lowest entropy value In case the corner studied contains chip No. 2, the forty-nine values of the logarithmic probability ratio $\lambda$ are very different. In fact, the more the processed sample g resembles the reference signal, the greater the value of $\lambda$. For the pixel corresponding to the exact center of chip No. 2, $\lambda(g)$ is therefore great, and the more one departs from that pixel, the less the value of $\lambda$. FIGS. 13A and 13B give the trend of $\lambda$ as a function of the position of pixel P in the search area of seven pixels per side. In FIG. 13A, a more or less marked peak is evident around the center of the chip. In FIG. 13B, it can be seen that in case the corner studied does not contain chip No. 2, the values of $\lambda$ are not ordinate and present no peak.

The peak shape on the values of $\lambda$ being more distinct for the corner containing chip No. 2 than for the others, it is therefore possible to identify it. For that purpose, an analogy is made with the concept of entropy of a signal. In fact, a signal whose histogram is flat has a higher entropy than a signal whose histogram contains a peak. The set of values of $\lambda$ is therefore standardized, so that the sum will be equal to 1, and then the entropy is calculated with the following formula:

$$h_k = \sum_{i,j=1}^{7} \lambda_{i,j,norm} \log_2(\lambda_{i,j,norm}), \text{ where } k \in \{1, \ldots, 4\}.$$

Concepts other than entropy can also be used. It is necessary to be able to characterize the representative surface of the set of probability values obtained on the search area. The area containing a peak contains the chip. Thus, instead of entropy, one can, in particular, use all of the measurements of roughness or texture index used in image processing.

Corner number $k_m$ such as $$h_{km} = \min_k(h_k)$$

is chosen as being the corner which contains chip No. 2.

Calculation of the proportion of correct detections on the set of images processed The algorithm comes, for example, in the form of IDL (Interface Definition Language) functions, and the results are stored in text files in order to be reused.

First results can thus be shown on the images of the CD MAM 3.2 phantom 10.

A first series of tests was carried out on images of the CD MAM 3.2 phantom 10, and the performances of the non-whitening filter were compared to the results obtained by radiologists on a clinical study.

As far as the experimental conditions are concerned, the images were acquired with the parameters presented in Table 2.

TABLE 2

Image Acquisition Parameters of CD MAM 3.2

| Series | Track/Filter | KV | mAs | Plexiglas thickness |
|---|---|---|---|---|
| 1 | Rh/Rh | 26 | 100 | 4.5 cm |
| 2 | Rh/Rh | 26 | 50 | 4.5 cm |
| 3 | Rh/Rh | 26 | 32 | 4.5 cm |
| 4 | Rh/Rh | 32 | 100 | 7.5 cm |
| 5 | Rh/Rh | 32 | 50 | 7.5 cm |
| 6 | Rh/Rh | 32 | 32 | 7.5 cm |

The acquisition parameters of series 1 and 4 are given by the automatic mode of the mammography machine, for example, the Senograph DMR™. The other series correspond respectively to 50% and 32% of the previous doses. That is explained by the fact that the clinical study involved a comparison of scores as a function of the detector (film or digital).

As far as the comparison with clinical data is concerned, FIGS. 14 to 16 show the performances of the non-whitening mathematical observer in relation to human observers for twenty-four images. Each curve represents the logarithmic minimal diameter (mm) as a function of the logarithmic gold thickness of the chips 3 (µm). The experimental conditions of the curves of FIGS. 14 to 16 are respectively 100 mAs, 45 mm of Plexiglas, 32 mAs, 45 mm of Plexiglas and 32 mAs, 75 mm of Plexiglas. The curves corresponding to the results of the radiologists are average.

FIG. 15 shows the inter-observer variability in performances of radiologists. The points on the curve of FIG. 17 correspond to the average response and the vertical lines represent the standard deviation. When the contrast is very low (small gold thicknesses), the human observers obtain very different results.

It can be observed, on comparing FIG. 14 and FIG. 15, that the performances of the mathematical observer are less affected than those of the human observer when the dose diminishes. On the other hand, they are more sensitive to the diffusion entailed in an increase of Plexiglas thickness, as FIG. 15 and FIG. 16 show. Nevertheless, in all the cases, the curves of the different observers have the same trend.

This initial study has made it possible to link the results obtained by the human observers and the mathematical observer. However, although the images observed were acquired under the same conditions, they are not the same. Furthermore, some points, such as the influence of calibration of the system of acquisition and the number of images processed, have to be explored more in detail.

The tests were continued with images of the CD MAM 3.4 phantom 10, which presents objects of interest smaller than the CD MAM 3.2. The images were acquired with the parameters described in Table 3.

TABLE 3

Image Acquisition Parameters of CD MAM 3.4

| Series | Calibration | Track/Filter | kV | mAs | Plexiglas thickness |
|---|---|---|---|---|---|
| 7 | Yes | Rh/Rh | 26 | 100 | 4.5 cm |
| 8 | Yes | Rh/Rh | 26 | 50 | 4.5 cm |
| 9 | Yes | Rh/Rh | 26 | 32 | 4.5 cm |
| 10 | Yes | Rh/Rh | 32 | 100 | 7.5 cm |
| 11 | Yes | Rh/Rh | 32 | 50 | 7.5 cm |
| 12 | Yes | Rh/Rh | 32 | 32 | 7.5 cm |
| 13 | No | Rh/Rh | 26 | 100 | 4.5 cm |
| 14 | No | Rh/Rh | 26 | 50 | 4.5 cm |
| 15 | No | Rh/Rh | 26 | 32 | 4.5 cm |
| 16 | No | Rh/Rh | 32 | 100 | 7.5 cm |
| 17 | No | Rh/Rh | 32 | 50 | 7.5 cm |
| 18 | No | Rh/Rh | 32 | 32 | 7.5 cm |

Applying the scoring algorithm to a set of images and not to a single image has two advantages.

First of all, the use of overall averages, particularly for construction of the reference signal, makes it possible to increase the signal to noise ratio, as shown in FIGS. 18A and 18B. The signal to noise ratio is greater in FIG. 18B than it is in FIG. 18A.

Comparison of the samples processed with the model thus created gives results all the better as the noise in the model is low. Furthermore, for a given cell, once the probability ratio is constructed, it is applied to all the images of the set. That operation makes it possible to estimate the performances of the mathematical observer on the cell processed. To understand that point well, the following three cases are considered:

1. If the cell 5 is situated in an area of the phantom 10 where the chips 3 have a large diameter and thickness, the detection of chip No. 2 is carried out correctly on all the images of the set. That case corresponds to the white boxes situated on the upper right of the images of FIGS. 19A and 19B (the results of FIG. 19A being the results before correction and the results of FIG. 19B being those after correction). Whether one or more images are processed, the result is the same.

2. If the cell 5 is situated in a region of the phantom 10 where the chips 3 have a small diameter and thickness, the mathematical observer does not detect chip No. 2. The choice of corner of the cell containing that chip is therefore made at random. There is one chance out of four of giving the good response. In that case, if only one image is processed, the box corresponding to that cell also has one chance out of four of being white. If a set of images is processed, the box will simply become hatched or double-hatched according to the code of FIG. 2. That phenomenon can be observed on the left on the images of FIGS. 19A and 19B.

3. If the cell 5 is situated in an area of the phantom 10 where the characteristics of the chips 3 render detection difficult but not impossible, it will be carried out correctly on some images, but not on all. The boxes corresponding to those cells are situated on the border of the two areas mentioned above, and their color varies with the number of images of the set.

The images of FIGS. 19A and 19B show the course of performances of the non-whitening filter as a function of the number of images.

The change of color of a box can have several meanings. A double-hatched box which becomes white when the number of images increases corresponds to an improvement of performances due to the increase in the signal to noise ratio. Otherwise, if a white box becomes double-hatched, that reveals an uncertainty about the detectability of chip No. 2. In fact, the more the number of images increases, the greater the chance that a chip 3 situated just at the limit of the correct detection area will not be located by the mathematical observer.

In cases 2 and 3 described above, the processing of just one image does not make it possible to draw a direct conclusion as to the detection of chip No. 2. It is necessary to apply the rules of correction several times in order to obtain a clear border between the correct and incorrect detection areas. On the other hand, for a given cell, the use of a set of images contributes information on the proportion of correct detections. It is possible to set a threshold on that proportion in order to decide whether chip No. 2 is considered correctly detected. That is what had been done in order to obtain the results on the images of the CD MAM 3.2. But the threshold value is arbitrary. On the other hand, that information can be used to construct a new decision criterion.

The new decision criterion consists of the use of confidence intervals on the proportion of correct detection. An advantageous variant of the scoring method already described in the previous embodiments is thus defined.

For a given cell 5, the proportion of correct detections of chip No. 2 is considered in relation to the number of images of the set. When the number of images increases, that proportion tends toward a value that will be called detection sensitivity for that cell 5. In order to elaborate a criterion making it possible to decide whether the result obtained by the mathematical observer is valid, confidence intervals are calculated on the proportion of correct detections.

The 95% confidence interval associated with the proportion of correct detections gives the limits between which the probability of finding the detection sensitivity is 0.95.

The confidence intervals were calculated with the Wilson method, which is appropriate for a small number of images. It is described by the following formula:

$$IC = \frac{X + k^2/2}{n + k^2} \pm \frac{kn^{1/2}}{n + k^2}\left(\hat{p}(1 - \hat{p}) + \frac{k^2}{4n}\right)^{1/2},$$

where X is the number of correct detections among the n images processed, p̂ is the proportion of correct detections, n is the number of images processed and k is the standard normal deviation.

A value of 1.96 is assigned to the standard normal deviation corresponding to the calculation of 95% confidence intervals.

One can therefore now speak of a choice of decision criterion on detection.

The case in which the detection of chip No. 2 is made completely at random is considered. Inasmuch as there is one chance out of four of choosing the right corner, the detection sensitivity is 0.25. The criterion it is sought to establish must make it possible to decide whether the mathematical observer has actually detected the chip. If that is the case, the detection sensitivity is greater than 0.25. The decision criterion chosen is therefore as follows: "If the lower limit of the 95% confidence interval is higher than 0.25, then chip No. 2 was detected by the mathematical observer."

FIG. 9A represents the cells well detected on all the images.

FIG. 20B represents the cells well detected with the new decision criterion.

FIGS. 20A and 20B show the performances of the non-whitening filter with the new decision criterion for a set of ten images. The widening of the correct detection area shows that the information contained in the cells displayed singly hatched in FIGS. 19A and 19B were taken into account on calculation of the confidence intervals.

A comparison is therefore now going to be made with new clinical data.

Influence of the Number of Images on the Results of the Mathematical Observer

FIGS. 21 (100 mAs, 45 mm of Plexiglas) and 22 (32 mAs, 45 mm of Plexiglas) show that the performances of the non-whitening filter improve when the number of images increases, particularly for a low-dose acquisition. In fact, increase of the signal to noise ratio makes possible a better detection of the small-sized chips. Furthermore, calculation of the confidence intervals is more precise, which enables a sharper decision to be made.

Influence of Dose on the Results of the Mathematical Observer

The curve of FIG. 23 corresponding to the images acquired at 32 mAs is situated above that of the images acquired at 100 mAs. That means that the well detected chips have a greater diameter when the dose diminishes. In fact, in that case, the contrast is weaker on the image and the small chips are more difficult to perceive.

Influence of Calibration on the Results of the Mathematical Observer

The influence of calibration was studied on images of the CD MAM 3.4 phantom 10 acquired with the same parameters and on the same mammography machine (see Table 3). Calibration of the digital detector was made between the acquisition of series 12 and 13. The parameters of FIGS. 24A and 24B are 12 images, 100 mAs and 45 mm of Plexiglas.

FIGS. 24A (before correction) and 24B (after correction) show in their upper part that the results obtained by the non-whitening filter on the images acquired on a poorly calibrated machine present a narrower white area at the top and bottom of the phantom. That means that the chips of larger and small diameter are less well detected. Consequently, the score obtained is not as good. On the other hand, the rules of correction had to be applied several times in succession before obtaining a smooth border profile by reason of the large number of cells correctly detected, but isolated, regardless of the number of images. This phenomenon occurs for images acquired on a well calibrated machine (lower part of FIGS. 24A and 24B) only as from a number of images in excess of ten.

Measurement of Performances of Human Observers

In order to compare the results obtained by the mathematical observer with those of human observers, an experiment was set up. Four of the images processed by the observer were selected.

Their conditions of acquisition are described in the following Table 4:

| Calibration | Track/Filter | kV | mAs | Plexiglas thickness |
|---|---|---|---|---|
| Yes | Rh/Rh | 26 | 100 | 4.5 cm |
| Yes | Rh/Rh | 26 | 32 | 4.5 cm |
| No | Rh/Rh | 26 | 100 | 4.5 cm |
| No | Rh/Rh | 26 | 32 | 4.5 cm |

Each of these images was read three times by each observer, in random order; five observers, two of whom were radiologists, participated in the experiment.

The reading was made on a review station, and the choice of corners containing the chips was registered by means of a software tool. The readers then observed the images one by one and clicked on the screen the cells situated at the limit of the chip visibility area.

Here is the statistical study of the results obtained by the human observers.

A variance analysis was made on the results by means of a software tool. For a given cell, the variability factors considered are, in decreasing order of importance: the observer, the calibration of the machine and the reading (which can be considered an implementation). The influence of calibration/reading interaction was also studied. Calibration and reading are fixed and crossed factors, and the observer is a random factor interlinked with calibration, insofar as any observer could be taken to extrapolate the study.

The variance analysis is made for a 95% confidence interval.

The variability introduced by each of the factors studied is considered significant when the associated p-value is less than 0.05. In fact, in that case, the probability of making a mistake by saying that the variability introduced by the factor studied is significant is less than 5%. Tables 5 and 6 below present the results given by the software. The first column ("source") lists the factors studied, and the parentheses indicate that two factors are interlinked. The last column ("P") gives the p-values associated with each factor.

TABLE 5

Variance analysis: images acquired at 100 mAs, 45 mm of Plexiglas
Variance analysis for Score

| Source | DF | SS | MS | F | P |
|---|---|---|---|---|---|
| Observer | 4 | 4.1933 | 1.0483 | 8.12 | 0.021 |
| Calibration (Observer) | 5 | 0.6452 | 0.1290 | 0.59 | 0.705 |
| Reading | 2 | 0.3749 | 0.1874 | 2.75 | 0.124 |
| Observer* Reading | 8 | 0.5458 | 0.0682 | 0.31 | 0.943 |
| Error | 10 | 2.1697 | 0.2170 | | |
| Total | 29 | 7.9289 | | | |

TABLE 6

Variance analysis: images acquired at 32 mAs, 45 mm of Plexiglas
Variance analysis for Score 2

| Source | DF | SS | MS | F | P |
|---|---|---|---|---|---|
| Observer | 4 | 8.7481 | 2.1870 | 15.96 | 0.005 |
| Calibration (Observer) | 5 | 0.6850 | 0.1370 | 0.91 | 0.512 |
| Reading 2 | 2 | 0.4431 | 0.2215 | 1.29 | 0.328 |
| Observer* Reading 2 | 8 | 1.3786 | 0.1723 | 1.14 | 0.413 |
| Error | 10 | 1.5079 | 0.1508 | | |
| Total | 29 | 12.7627 | | | |

One finds that the observer factor has a p-value less than 0.05. It is therefore the only significant source of variability. The second table gives the same results, but more accentuated, for a low dose.

A comparison can thus be made among the results of the different observers.

Considering that the variability introduced by the change of observer is very substantial, the performances of the mathematical observer are compared with those of an average human observer by indicating the standard deviation on the results of the readers.

Figure 25:
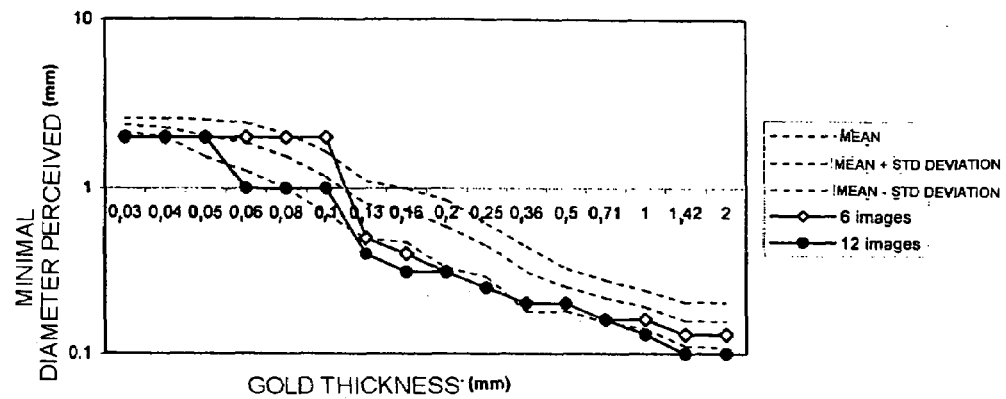
FIG. 25 shows schematically a comparison of the observers for 100 mAs and a calibrated machine.
Figure 26:
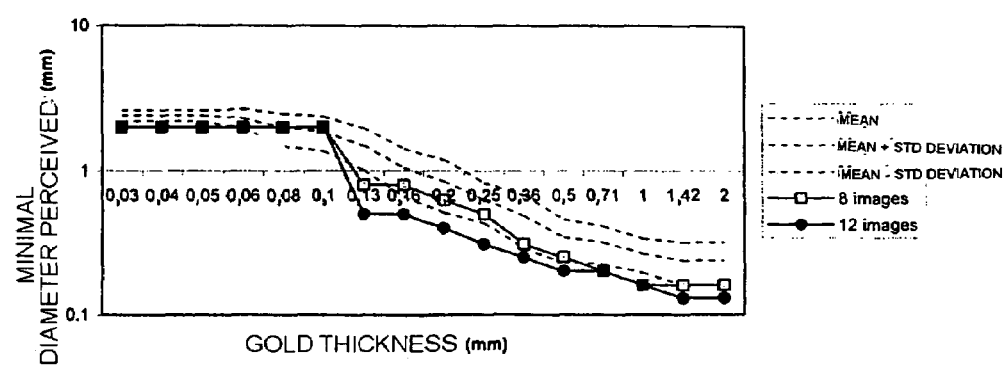
FIG. 26 shows schematically a comparison of the observers for 32 mAs and a calibrated machine.

In FIG. 24 and FIG. 25, the dotted lines correspond to the values of the diameters correctly detected by the human observers (mean−standard deviation, mean, mean+standard deviation). The other curves represent the results of the mathematical observer following the number of images of the set. The curves of the human readers are smoother by reason of the averaging done on the data. On the other hand, for low gold thicknesses, the mathematical observer detects chips whose diameters belong to the set (2; 1.6; 1.25; 1; 0.8), which gives a "staircase" appearance to the curve.

One finds that the results of the mathematical observer are situated under the "mean+standard deviation" curve of the results of the human observers for twelve images, regardless of the dose. However, the improvement previously mentioned, when the number of images is increased, is more sensitive to the level of strong contrasts (gold thickness exceeding 0.16 μm). One can therefore envisage further increasing the number of images in order to improve the correlation between the results of the human observers and of the non-whitening filter, particularly for weak contrasts. However, one should not lose sight of the fact that the performances of the human readers are highly variable, particularly for the ends of the phantom, that is, for the very strong and very weak contrasts. Under those conditions, the use of a mathematical observer offers the advantage of supplying reproducible results, close to those of an average human observer in the central part of the phantom and of the same trend for the ends.

Summary of the disclosed method and embodiments:
1. Detection of the coordinates of the phantom cells
2. For each phantom cell:
   a. Calculation of the reference signal $\overline{g}_a - \overline{g}_b$
   b. For each cell corner:
   c. Definition of a set of $N_c$ centers P of the area of interest for the current corner and for each pixel P:
      (i). Extraction of a sample g corresponding to an area of interest centered on P
      (ii). Calculation of the logarithmic probability function $\lambda_{NPW}(g) - (\overline{g}_a - \overline{g}_b)^t g$,
   d. Calculation of the entropy of the set of $N_c$ values λ thus obtained
   e. Selection of the area of interest of minimal entropy
   f. Calculation of the proportion of correct detections from a set of N images processed: a satisfactory detection is validated if the lower limit of the confidence interval at a given value, 95%, for example, is higher than a threshold value, above 0.25, for example.
3. Use of the standard rules of correction of the CD-MAM phantom
4. Calculation of the IQF (Image Quality Factor) score from the results of detection for all of the cells of the phantom.

Stages c, d and e make it possible to locate the gold disk of the current cell in case the real and exact position of the disk does not correspond to specifications. That effect was observed and affects the score calculation performances, particularly in the case of the smallest disks. The search in a neighborhood around the theoretical position of the disk (of size $N_c$ pixels) reduces the risks of missing the disk. In that way, the corners without chip lead to sets of values of λ that are "flat", while the corner containing the chip leads to a set of values of λ containing a peak. The calculation of entropy of the sets of values λ for each corner therefore makes it possible to detect the corner possessing the gold disk, for the entropy of the λ set for that corner is minimal. Those different stages make it possible to improve the sensitivity and reliability of the score calculation.

Stage f renders the decision more reliable. If we used only one image, we could decide by chance that the chip detection is correct in a given cell of the phantom. The use of several images acquired under identical conditions makes it possible to capture the variations of X-ray physics (quantum fluctuations), so that a chip may not be detected on each image. For each cell, we estimate from N images the proportion of correct detections. From the associated confidence interval (at 95%, for example), we can decide, for instance, whether the chip has actually been detected if its lower limit exceeds 0.25 (1 chance out of 4 of locating the chip in one of the corners).

One skilled in the art may propose or make various modifications in the structure and/or function and/or result and/or way to the disclosed embodiments and equivalents thereof without departing from the scope and extent of the invention.

The invention claimed is:
1. A method of evaluation of the quality of at least one radiographic image of a phantom containing a plurality of cells, at least one of which contains two objects visualizable by radiography, the position in the cell of at least one of the objects being known, and the position in the cell of the other object being random from one cell to another comprising:

19 a. determining the coordinates of each phantom cell on each phantom image containing at least two objects;
b. calculating a level of a radiographic reference signal in an area of reference at right angles with the first object whose position in the cell is known;
c. for each area of the cell capable of containing the other object:
   (1) a search area formed by a set of pixels is defined;
   (2) for each pixel of the search area:
d. extracting a signal sample in an area of interest centered on the pixel and of the same size as the reference area;
   (1) calculating a probability parameter between the sample and the reference signal, the probability function corresponding to a mathematical observer to obtain a parameter characterizing the trend of the representative surface of the set of probability values;
e. selecting the area of interest whose surface presents the trend of a peak as area containing the other object; and
f. calculating an image quality score from the results of detection for the set of phantom cells.

2. The method according to claim 1 wherein when it is desired to evaluate the quality of a set of images, after selection of the area containing a minimal entropy and before calculation of the image quality score, comprising:
   a. calculating a proportion of correct detections from a set of processed image;
   b. calculating a confidence interval around that proportion of correct detections;
   c. declaring a detection valid if the lower limit of the confidence interval is higher than a threshold value; and
   d. using standard rules of correction for the phantom.

3. The method according to claim 1 wherein to obtain the level of the radiographic reference signal comprising:
   a. selecting the reference area of the image containing the first object by centering it on the center of the object, the diameter of the reference area being slightly greater than that of the object;
   b. selecting a background area of the image of the same size as the reference area on a region of the cell that can in no case contain any object;
   c. taking an overall average of the signals selected for each of these areas; and
   d. subtracting the average signal of the background area from the average signal of the reference area.

4. The method according to claim 1 wherein the probability parameter is a logarithmic probability function corresponding to a non-whitening observer on the search area, the function being defined by the formula:

$$\lambda_{NPW}(g)=(\overline{g}_a-\overline{g}_b)^t g,$$

where g is the signal of the image sample in the search area, $\overline{g}_a$ is the average signal of the reference area and $\overline{g}_b$ is the average signal of the background area.

5. The method according to claim 1 wherein the parameter characterizing the trend of the surface is an entropy parameter, which is defined for each area k by the formula $$h_k = \sum_{i,j=1}^{L} \lambda_{i,j,norm} \log_2(\lambda_{i,j,norm}), \text{ avec } k \in \{1, \ldots, N\},$$

where k is the reference of the area of the cell capable of containing the other object, $\lambda_{i,j,norm}$ is the standardized logarithmic probability value calculated for the pixel (i, j) of the search area and L is the number of pixels of the search area.

6. The method according to claim 2 wherein the limits of the confidence interval are calculated by the formula:

$$IC = \frac{X+k^2/2}{n+k^2} \pm \frac{kn^{1/2}}{n+k^2}\left(\hat{p}(1-\hat{p}) + \frac{k^2}{4n}\right)^{1/2},$$

where X is the number of correct detections among the n images processed, $\hat{p}$ is the proportion of correct detections, n is the number of images processed and k is the standard normal deviation.

7. The method of claim 6 wherein a value of 1.96 is assigned to the standard normal deviation corresponding to the calculation of 95% confidence intervals.

8. The method according to claim 2 wherein the value of 0.25 is assigned to the threshold value.

9. The method according to claim 1 wherein at least one image of a phantom containing two chips in each cell is observed, the cells being rectangular, a first chip being situated in the center of each cell, the other chip being randomly situated from one cell to the other in one of the four corners of each cell.

10. A device for evaluation of the quality of at least one radiographic image of a phantom containing a plurality of cells, at least one of which contains two objects visualizable by radiography, the position in the cell of at least one of the objects being known, and the position in the cell of the other object being random, wherein the device comprises:
    a. means for determining on each phantom image the coordinates of each phantom cell;
    b. means for each phantom cell containing at least two objects;
    c. means for calculating the level of a radiographic reference signal in an area of reference at right angles with the first object whose position in the cell is known;
    d. means for each area of the cell capable of containing the other object:
    e. means for defining a search area formed by a set of pixels;
    f. means for each pixel of the search area:
       (1) extracting a signal sample in an area of interest centered on the pixel and of the same size as the reference area; and
       (2) calculating the logarithmic probability function between the sample and the reference signal, the probability function corresponding to a mathematical observer;
    g. means for selecting as area containing the other object the area of interest whose surface presents the trend of a peak; and
    h. means for calculating the image quality score from the results of detection for the set of phantom cells.

11. The device according to claim 10 comprising:
    a. means for observing several phantom images;
    b. means for calculating the proportion of correct detections from a set of processed images;
    c. means for calculating a confidence interval around that proportion of correct detections;
    d. means for declaring a detection as valid if the lower limit of the confidence interval is higher than a threshold value; and
    e. means for applying standard rules of correction of the phantom.

12. The device according to claim 10 wherein the device is mounted on a radiographic image acquisition device.

13. A program storage device readable by a machine, tangibly embodying a program of instructions executable by the machine to perform method steps on a radiographic image acquisition device for the evaluation of the quality of at least one radiographic image of a phantom containing a plurality of cells, at least one of which contains two objects visualizable by radiography, the position in the cell of at least one of the objects being known, and the position in the cell of the other object being random from one cell to another, the method steps comprising:
   a. determining the coordinates of each phantom cell on each phantom image containing at least two object;
   b. calculating a level of a radiographic reference signal in an area of reference at right angles with the first object whose position in the cell is known;
   c. for each area of the cell capable of containing the other object:
      (1) a search area formed by a set of pixels is defined;
      (2) for each pixel of the search area:
   d. extracting a signal sample in an area of interest centered on the pixel and of the same size as the reference area;
      (1) calculating a probability parameter between the sample and the reference signal, the probability function corresponding to a mathematical observer to obtain a parameter characterizing the trend of the representative surface of the set of probability values;
   e. selecting the area of interest whose surface presents the trend of a peak as area containing the other object; and
   f. calculating an image quality score from the results of detection for the set of phantom cells.

14. The method according to claim 2 wherein to obtain the level of the radiographic reference signal comprising:
   a. selecting the reference area of the image containing the first object by centering it on the center of the object, the diameter of the reference area being slightly greater than that of the object;
   b. selecting a background area of the image of the same size as the reference area on a region of the cell that can in no case contain any object;
   c. taking an overall average of the signals selected for each of these areas; and
   d. subtracting the average signal of the background area from the average signal of the reference area.

15. The method according to claim 2 wherein the probability parameter is a logarithmic probability function corresponding to a non-whitening observer on the search area, the function being defined by the formula:

$$\lambda_{NPW}(g)=(\overline{g}_a-\overline{g}_b)^t g,$$

where g is the signal of the image sample in the search area, $\overline{g}_a$ is the average signal of the reference area and $\overline{g}_b$ is the average signal of the background area.

16. The method according to claim 3 wherein the probability parameter is a logarithmic probability function corresponding to a non-whitening observer on the search area, the function being defined by the formula:

$$\lambda_{NPW}(g)=(\overline{g}_a-\overline{g}_b)^t g,$$

where g is the signal of the image sample in the search area, $\overline{g}_a$ is the average signal of the reference area and $\overline{g}_b$ is the average signal of the background area.

17. The method according to claim 2 wherein the parameter characterizing the trend of the surface is an entropy parameter, which is defined for each area k by the formula $$h_k = \sum_{i,j=1}^{L} \lambda_{i,j,norm} \log_2(\lambda_{i,j,norm}), \text{ avec } k \in \{1, \ldots, N\},$$

where k is the reference of the area of the cell capable of containing the other object, $\lambda_{i,j,norm}$ is the standardized logarithmic probability value calculated for the pixel (i, j) of the search area and L is the number of pixels of the search area.

18. The method according to claim 3 wherein the parameter characterizing the trend of the surface is an entropy parameter, which is defined for each area k by the formula $$h_k = \sum_{i,j=1}^{L} \lambda_{i,j,norm} \log_2(\lambda_{i,j,norm}), \text{ avec } k \in \{1, \ldots, N\},$$

where k is the reference of the area of the cell capable of containing the other object, $\lambda_{i,j,norm}$ is the standardized logarithmic probability value calculated for the pixel (i, j) of the search area and L is the number of pixels of the search area.

19. The method according to claim 4 wherein the parameter characterizing the trend of the surface is an entropy parameter, which is defined for each area k by the formula $$h_k = \sum_{i,j=1}^{L} \lambda_{i,j,norm} \log_2(\lambda_{i,j,norm}), \text{ avec } k \in \{1, \ldots, N\},$$

where k is the reference of the area of the cell capable of containing the other object, $\lambda_{i,j,norm}$ is the standardized logarithmic probability value calculated for the pixel (i, j) of the search area and L is the number of pixels of the search area.

20. The method according to claim 3 wherein the limits of the confidence interval are calculated by the formula:

$$IC = \frac{X+k^2/2}{n+k^2} \pm \frac{kn^{1/2}}{n+k^2}\left(\hat{p}(1-\hat{p})+\frac{k^2}{4n}\right)^{1/2},$$

where X is the number of correct detections among the n images processed, $\hat{p}$ is the proportion of correct detections, n is the number of images processed and k is the standard normal deviation.

21. The method according to claim 4 wherein the limits of the confidence interval are calculated by the formula:

$$IC = \frac{X+k^2/2}{n+k^2} \pm \frac{kn^{1/2}}{n+k^2}\left(\hat{p}(1-\hat{p})+\frac{k^2}{4n}\right)^{1/2},$$

where X is the number of correct detections among the n images processed, $\hat{p}$ is the proportion of correct detections, n is the number of images processed and k is the standard normal deviation.

22. The method according to claim 5 wherein the limits of the confidence interval are calculated by the formula:

$$IC = \frac{X + k^2/2}{n + k^2} \pm \frac{kn^{1/2}}{n + k^2}\left(\hat{p}(1 - \hat{p}) + \frac{k^2}{4n}\right)^{1/2},$$

where X is the number of correct detections among the n images processed, $\hat{p}$ is the proportion of correct detections, n is the number of images processed and k is the standard normal deviation.

23. The method according to claim 3 wherein a value of 1.96 is assigned to the standard normal deviation corresponding to the calculation of 95% confidence intervals.

24. The method according to claim 4 wherein a value of 1.96 is assigned to the standard normal deviation corresponding to the calculation of 95% confidence intervals.

25. The method according to claim 5 wherein a value of 1.96 is assigned to the standard normal deviation corresponding to the calculation of 95% confidence intervals.

26. The method according to claim 3 wherein the value of 0.25 is assigned to the threshold value.

27. The method according to claim 4 wherein the value of 0.25 is assigned to the threshold value.

28. The method according to claim 5 wherein the value of 0.25 is assigned to the threshold value.

29. The method according to claim 6 wherein the value of 0.25 is assigned to the threshold value.

30. The method according to claim 7 wherein the value of 0.25 is assigned to the threshold value.

31. The method according to claim 2 wherein at least one image of a phantom containing two chips in each cell is observed, the cells being rectangular, a first chip being situated in the center of each cell, the other chip being randomly situated from one cell to the other in one of the four corners of each cell.

32. The method according to claim 3 wherein at least one image of a phantom containing two chips in each cell is observed, the cells being rectangular, a first chip being situated in the center of each cell, the other chip being randomly situated from one cell to the other in one of the four corners of each cell.

33. The method according to claim 4 wherein at least one image of a phantom containing two chips in each cell is observed, the cells being rectangular, a first chip being situated in the center of each cell, the other chip being randomly situated from one cell to the other in one of the four corners of each cell.

34. The method according to claim 5 wherein at least one image of a phantom containing two chips in each cell is observed, the cells being rectangular, a first chip being situated in the center of each cell, the other chip being randomly situated from one cell to the other in one of the four corners of each cell.

35. The method according to claim 6 wherein at least one image of a phantom containing two chips in each cell is observed, the cells being rectangular, a first chip being situated in the center of each cell, the other chip being randomly situated from one cell to the other in one of the four corners of each cell.

36. The method according to claim 7 wherein at least one image of a phantom containing two chips in each cell is observed, the cells being rectangular, a first chip being situated in the center of each cell, the other chip being randomly situated from one cell to the other in one of the four corners of each cell.

37. The method according to claim 8 wherein at least one image of a phantom containing two chips in each cell is observed, the cells being rectangular, a first chip being situated in the center of each cell, the other chip being randomly situated from one cell to the other in one of the four corners of each cell.

38. The device according to claim 11 wherein the device is mounted on a radiographic image acquisition device.

39. An article of manufacture for use in a computer system, the article of manufacture comprising a computer useable medium having computer readable program code means embodied in the medium, the program code means evaluating the quality of at least one radiographic image of a phantom containing a plurality of cells, at least one of which contains two objects visualizable by radiography, the position in the cell of at least one of the objects being known, and the position in the cell of the other object being random from one cell to another, the program code means including:

a. computer readable program code means embodied in the computer usable medium for causing the computer to effect a determination of the coordinates of each phantom cell on each phantom image containing at least two objects;

b. computer readable program code means embodied in the computer usable medium for causing the computer to calculate a level of a radiographic reference signal in an area of reference at right angles with the first object whose position in the cell is known;

c. computer readable program code means embodied in the computer usable medium for causing the computer for each area of the cell capable of containing the other object to define a search area formed by a set of pixels;

d. computer readable program code means embodied in the computer usable medium for each pixel of the search area extracting a signal sample in an area of interest centered on the pixel and of the same size as the reference area;

e. computer readable program code means embodied in the computer usable medium for calculating a probability parameter between the sample and the reference signal, the probability function corresponding to a mathematical observer to obtain a parameter characterizing the trend of the representative surface of the set of probability values;

f. computer readable program code means embodied in the computer usable medium for selecting the area of interest whose surface presents the trend of a peak as area containing the other object; and g. computer readable program code means embodied in the computer usable medium for calculating an image quality score from the results of detection for the set of phantom cells.

* * * * *